US005747461A

United States Patent [19]

Markov

[11] Patent Number: 5,747,461
[45] Date of Patent: May 5, 1998

[54] SYNERGISTIC ADMINISTRATION OF CYCLOSPORINE AND FRUCTOSE DIPHOSPHATE

[76] Inventor: Angel K. Markov, 5973 Hanging Moss Rd., Jackson, Miss. 39206

[21] Appl. No.: 280,374

[22] Filed: Jul. 26, 1994

[51] Int. Cl.$^6$ .................................................. A61K 31/70
[52] U.S. Cl. .......................... 514/23; 514/9; 514/25; 514/885; 514/922; 530/317
[58] Field of Search ...................... 514/23, 9, 25, 514/885, 922; 530/317

[56] References Cited

U.S. PATENT DOCUMENTS

| | | | |
|---|---|---|---|
| 4,448,771 | 5/1984 | Cattani et al. | 424/180 |
| 4,546,095 | 10/1985 | Markov | 514/23 |
| 4,757,052 | 7/1988 | Markov | 514/23 |
| 4,916,220 | 4/1990 | Galzigna et al. | 536/117 |
| 5,039,655 | 8/1991 | Markov | 514/23 |
| 5,039,665 | 8/1991 | Markov | 514/23 |
| 5,196,402 | 3/1993 | Braganza et al. | 514/46 |

FOREIGN PATENT DOCUMENTS

| | | |
|---|---|---|
| 3323850 | 1/1985 | Germany. |
| 9001938 | 8/1990 | WIPO. |

*Primary Examiner*—James O. Wilson
*Attorney, Agent, or Firm*—Patrick D. Kelly

[57] ABSTRACT

This invention discloses a method of using fructose-1,6-diphosphate (FDP) to help suppress the rejection of internal organs such as kidneys, hearts, etc. At least three major advantages of FDP in conjunction with organ transplants have been identified: (1) FDP can help reduce the unwanted proliferation of certain types of stimulated lymphocytes which would otherwise pose a risk of attacking the non-self cells in the transplanted organ; (2) FDP can also potentiate the effectiveness of cyclosporine as a transplant-protecting immunosuppressant, thereby allowing a reduction in CSA dosages, which in turn can reduce the likelihood and the severity of toxic side effects and other dangers of CSA treatment; (3) FDP can also reduce the amount of damage inflicted on an organ during the removal and storage steps required in organ transplantation.

3 Claims, 3 Drawing Sheets

SYNERGISTIC ADMINISTRATION OF CYCLOSPORINE AND FRUCTOSE DIPHOSPHATE

BACKGROUND OF THE INVENTION

This invention relates to the use of fructose-1,6-diphosphate, a naturally-occurring mammalian metabolite, in the preservation and transplantation of internal organs such as hearts and kidneys.

Fructose-1,6-diphosphate is one of the intermediate compounds that is created and then consumed in the metabolic process of glycolysis (the process by which energy is generated inside cells via the oxidation of glucose). Briefly, under conditions with adequate supplies of oxygen and adenosine triphosphate (ATP), glucose is phosphorylated into glucose-6-phosphate by a hexokinase enzyme; this phosphorylation step takes one of the phosphate groups from an adenosine triphosphate (ATP) molecule, converting the ATP molecule into adenosine diphosphate (ADP). In the second step, glucose-6-phosphate is converted from a six-member pyranose ring structure (or its tautomeric straight aldose chain) into a five-member furanose ring structure (or its tautomeric straight ketose chain) by a phosphoglucose isomerase enzyme. In the third step, a second phosphate group is taken from another ATP molecule and coupled to the #1 carbon atom by a phosphofructokinase enzyme (abbreviated as PFK), to create fructose-1,6-diphosphate, which is abbreviated herein as FDP.

In subsequent steps which use FDP as a substrate and consume it in the process, an FDP molecule (which has 6 carbon atoms) is broken into two smaller molecules with three carbons each (glyceraldehyde and dihydroxyacetone), in a reaction catalyzed by an aldolase enzyme.

These reactions, and various additional steps in aerobic and anaerobic glycolysis, are discussed in nearly any textbook on biochemistry or physiology; see, e.g., L. Stryer, *Biochemistry*, pp. 260–261 (second edition, 1981) or A. C. Guyton, *Medical Physiology*, pp. 841–842 (sixth edition, 1981).

When cells are deprived of adequate oxygen or ATP, the glycolytic pathway cannot sustain the relatively efficient process of aerobic glycolysis, and the glycolytic pathway is diverted to a condition of anaerobic glycolysis, which leads to the formation of lactic acid and to a condition called acidosis. Anaerobic glycolysis is not nearly as efficient or desirable as aerobic glycolysis. It can occur in response to numerous types of stress conditions, such as (in relatively mild form) in the muscles of athletes during exercise. It also occurs in much more severe form under conditions of ischemia (i.e., inadequate blood flow, as occurs during a stroke, heart attack, cardiac arrest, etc.) or other forms of hypoxia (i.e., inadequate oxygen supply, which occurs during ischemia and various other conditions such as suffocation, asphyxia, carbon monoxide poisoning, etc.).

Although anaerobic glycolysis is not nearly as desirable or efficient as aerobic glycolysis, it can become a vital and essential backup system under conditions of ischemia/hypoxia, since it generates at least some ATP molecules. Each molecule of FDP contributes to the conversion of 4 molecules of energy-poor ADP into energy-rich ATP during anaerobic glycolysis.

In prior work, the Applicant herein has shown that FDP can be used to treat various medical conditions. In U.S. Pat. No. 4,546,095, Dr. Markov disclosed that FDP can reduce myocardial infarction (i.e., the permanent tissue damage that occurs in heart muscle during heart attacks or certain other conditions). In U.S. Pat. No. 4,703,040, Dr. Markov disclosed that FDP could be used to treat mammals suffering adult respiratory distress syndrome (ARDS). And in U.S. Pat. No. 4,757,052, Dr. Markov disclosed that FDP can be used beneficially during the preservation of blood during storage.

All three of those prior art patents showed that injection of FDP helps alleviate various conditions by effectively bypassing certain "bottlenecks" and providing badly needed energy supplies to oxygen-starved cells. Unlike glucose molecules, which must be transported into cell interiors using a mechanism that requires insulin and energy, FDP can permeate directly into cells without requiring an energy-dependent transport mechanism. In addition, direct injection of exogenous FDP allows the glycolytic pathway to bypass the PFK enzyme, which converts fructose monophosphate into fructose diphosphate. The PFK enzyme can become fouled or poisoned under conditions of lactic acidosis; this inactivation of the enzyme prevents the creation of FDP. Since injection of FDP into the bloodstream of patients suffering from such problems bypasses these two bottlenecks (the cell transport bottleneck, and the PFK bottleneck), it provides starving cells with an energy-rich metabolite that can supply the glycolytic pathway and allow starving cells to sustain a limited form of metabolism through anaerobic glycolysis, until the preferred form of aerobic glycolysis can be restored. It also appears that providing exogenous FDP to the system as a substrate can help reduce or reverse any fouling of the PFK enzyme; this helps restore the PFK enzyme to an active status, so it can participate again in the glycolytic pathway.

The subject invention involves a new discovery, which is not directly related to the prior work involving ischemia, hypoxia, or other adverse conditions that can be treated by FDP as previously disclosed.

It has recently been discovered that, in addition to supplying the glycolytic pathway, FDP also has been discovered to reduce and control various cellular reactions that otherwise aggravate the rejection of internal organs in recipients of transplanted organs (such as kidneys, hearts, etc.). Various mechanisms appear to be involved; in particular, FDP can reduce the proliferation of certain types of stimulated lymphocytes which contribute to and aggravate the problem of organ rejection.

The following section provides additional background information on the cells and processes involved in the rejection of transplanted organs.

Organ Rejection; Stimulated T-Lymphocytes

An important function of cell membranes is to provide each cell with an "identity card" consisting of specific chemical groups, usually known as histocompatibility or transplantation antigens. Many transplantation antigens have been identified, and their polymorphisms is such that the probability of two individuals having the same combination is practically nil except in identical twins. The transplantation antigens are continuously surveyed by the lymphocytes, which have the ability to recognize the chemical groups on the surfaces of any "non-self" cells, which are treated as invaders of the organism.

The two major types of lymphocytes are classed as B cells and T cells; they were given these names because T cells are pre-processed in the thymus, while B cells were initially identified as being preprocessed in the so-called "bursa of Fabricius" in birds. In general, B lymphocytes participate in the rejection process by producing antibodies that bind specifically to antigens on the surfaces of their target. These antibodies produced by B cells do not kill by themselves; instead, they serve as recognition devices (markers) for other cells such as polymorphonuclear leukocytes, which kill the target cells. The antibodies also activate the "complement" system, which uses activated enzymes to attack and kill antibody-labelled cells.

In contrast to B cells, T cells attack non-self cells via direct contact mechanisms, by binding to antigens on the surfaces of the non-self cells and then carrying out various processes such as releasing cytotoxic substances into the invading cells, and releasing substances that attract and activate macrophage cells which migrate to the site and engulf and digest the non-self cells.

Another distinction between B and T cells is that B cells are often said to participate in "humoral" immunity; by contrast, T cells participate in "cellular" immunity. In general, humoral (B cell) immunity tends to be more rapid, and its effects do not last as long; it usually takes a primary role in defending against most bacterial infections. By contrast, cellular (T cell) immunity often takes a primary role in defending against infections that progress more slowly (such as tuberculosis), in defending against cancer, and in attacking the foreign cells of transplanted organs.

The relevant processes involving B cells, T cells, and other aspects of immune responses and organ rejection are discussed in numerous texts; useful overviews are provided in, e.g., Guyton's *Medical Physiology* (cited above) at pages 74–81.

When it occurs in response to organ transplantation, the rejection process is often referred to as an "allograft" reaction (the prefix "allo-" indicates that the material being grafted into the body of the host is foreign). This rejection reaction is any transplant surgeon's greatest source of frustration: no matter how well-suited the surgical techniques are or how close the tissue match may be, allograft rejection poses a relentless and lifelong threat to the patient.

A crucial step in the rejection process involves the activation of T cells in a manner that causes activated T cells (also referred to as stimulated T cells, or sensitized T cells) to recognize and attack cells having one or more non-self antigens on their surfaces. The activation signal is believed to involve a reaction between a non-self antigen and a T cell surface receptor; these receptors are probably glycoprotein molecules which straddle the membranes of the T cells. Relatively little is known about the molecular mechanisms by which a T-cell responds to an activation signal; although the sequence of events is known to result in certain morphological changes involving the transformation and proliferation of lymphoblasts (immature lymphocyte cells which give rise to mature differentiated lymphocytes), not much is known about the energy and entropic state of a T cell undergoing this transformation. Despite extensive research which has been published in the scientific and medical literature, not much is known about such parameters or how or why they change following T-cell activation.

Immunosuppressive Drugs

To attenuate rejection reactions, surgeons employ immunosuppressive agents in order to suppress immune responses in the organ recipient. Ideally, a perfect immunosuppressive agents would reduce the intensity of the allograft reaction, but without altering other forms of immune response, which remain necessary to enable the patient to resist bacterial, viral, and other infections.

At present, such an ideal immunosuppressive agent is not available. Most immunosuppressive agents currently being used reduce the body's ability to resist bacterial or viral infection, and can have other undesirable side effects as well. When used in high doses, these agents are toxic for immune cells and various other types of cells; however, if the dose is lower, they are less effective (or even ineffective) in preventing rejection of the transplanted organ.

Briefly, there are 4 groups of immunosuppressive agents: alkylating agents, antimetabolites (such as folic acid, or pyrimidine and purine analogues), steroids, and antibiotics.

The most promising and widely used immunosuppressive agent is cyclosporine A (abbreviated as CSA), which has specific action in suppressing antigen-stimulated T lymphocytes without interfering with B-cell activity. Since the introduction of CSA as an immunosuppressant, organ transplantation has become a much more successful procedure and has been used to prolong the lives of many thousands of patients.

However, CSA leaves much to be desired as an immunosuppressant. One of its major toxic manifestations involves the kidneys; renal (nephro) toxicity occurs in 20–25% of the allograft recipients treated with the drug. Renal toxicity, which is dose-related, is sometimes reversible, but it frequently requires discontinuation of CSA, a reduction in dosage, or other modifications of the therapy. Hypertension is also a major problem, encountered in about 30% of the patients who receive renal (kidney), hepatic (liver), or cardiac (heart) transplants and who are treated with CSA. Neurological CSA toxicity is also common, especially in patients with liver transplants.

In addition to disclosing that FDP by itself can help reduce organ rejection, this invention also discloses that FDP can also act in a synergistic manner to increase (potentiate) the effectiveness of cyclosporine as a transplant-protecting immunosuppressant. Accordingly, FDP can be used as an adjunct during CSA therapy to reduce the dosages of CSA, which in turn can reduce the likelihood and the severity of the toxic side effects and other dangers of CSA treatment.

It should be noted that a number of agents (including certain calcium channel blockers such as nicardipine and diltiazem, two vasodilators used to control anginal pain or reduce blood pressure) are widely used to increase the levels of CSA circulating in the blood of transplant recipients. This allows physicians to administer lower doses of CSA while still reaching desired blood levels. There is no reason to believe FDP works by that mechanism (i.e., by increasing CSA levels in the blood), and the in vitro data provided below suggests that FDP acts by an entirely different mechanism; instead of increasing blood concentrations of CSA, FDP appears to increase the T-cell controlling efficacy of whatever concentration of CSA is in the blood.

It has also been shown that FDP can reduce the amount of damage an organ suffers during transplantation, during the steps of removal, storage, and implantation. These activities were previously speculated by the Applicant based on FDP's other beneficial activities, but these activities had not been documented, quantified, or claimed in any of the prior patents issued to the Applicant (cited above).

Accordingly, one object of this invention is to disclose a method of utilizing FDP to help reduce and control various cellular reactions involved in the rejection of internal organs in recipients of transplanted organs.

Another object of this invention is to disclose a method of utilizing FDP to help reduce the unwanted proliferation of certain types of lymphocytes which contribute to rejection problems in organ transplantations.

Another object of this invention is to disclose a method of utilizing FDP as an adjunct during cyclosporine therapy after an organ transplant, to potentiate the desired immunosuppressing effectiveness of cyclosporine, thereby allowing a reduction in CSA dosages, which in turn can reduce the likelihood and the severity of toxic side effects and other dangers of CSA treatment.

Another object of the invention is to disclose that FDP reduces the amount of damage suffered by an organ during the removal and storage steps that are required during organ transplantation.

These and other objects of this invention will become apparent in the following summary and detailed description of the invention.

SUMMARY OF THE INVENTION

This invention discloses a method of using fructose-1,6-diphosphate (FDP) to help suppress the rejection of internal organs such as kidneys, hearts, etc. At least three major advantages of FDP in conjunction with organ transplants have been identified: (1) FDP can help reduce the unwanted proliferation of certain types of stimulated lymphocytes which would otherwise pose a risk of attacking the non-self cells in the transplanted organ; (2) FDP can also potentiate the effectiveness of cyclosporine as a transplant-protecting immunosuppressant, thereby allowing a reduction in CSA dosages, which in turn can reduce the likelihood and the severity of toxic side effects and other dangers of CSA treatment; (3) FDP can also reduce the amount of damage inflicted on an organ during the removal and storage steps required in organ transplantation.

DESCRIPTION OF THE PREFERRED EMBODIMENTS

Figure 1:
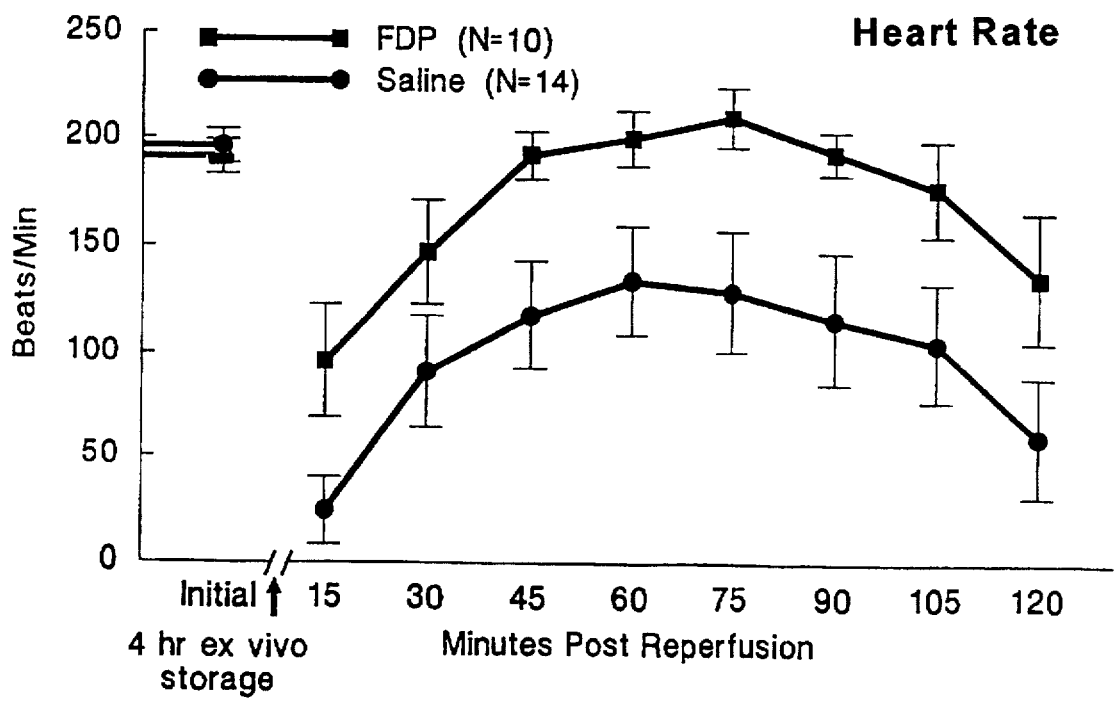
FIG. 1 is a graph depicting the improvement in heartbeat rate which was provided by FDP treatment, in hearts stored ex vivo for 4 hours in cold saline solution.
Figure 2:
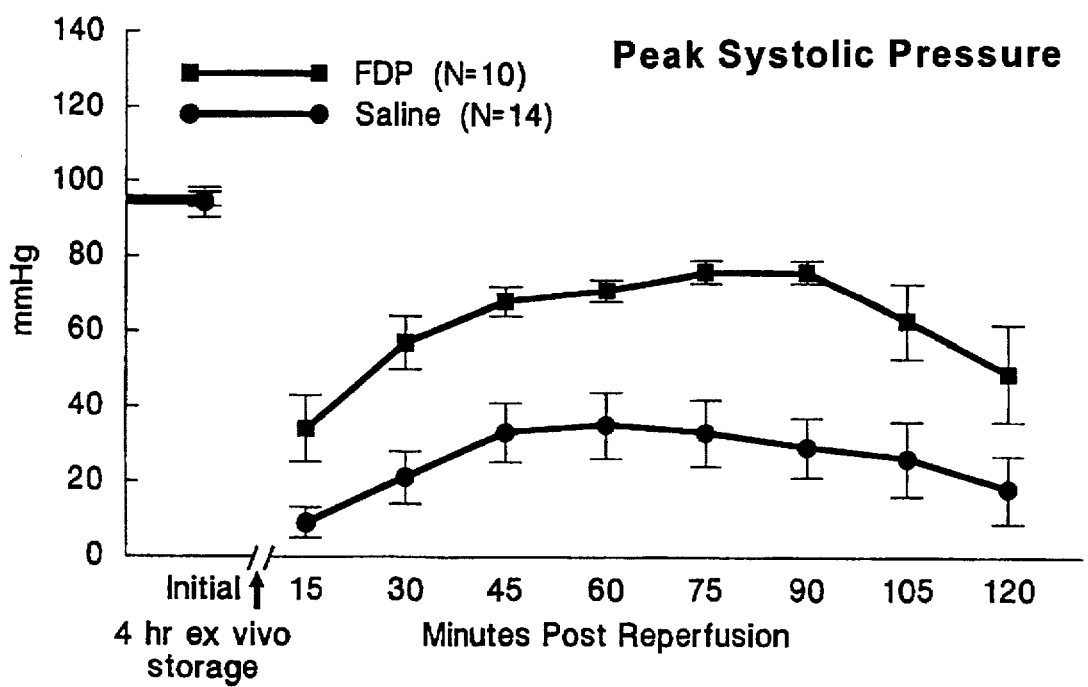
FIG. 2 is a graph depicting the improvement in peak systolic pressures provided by FDP treatment.
Figure 3:
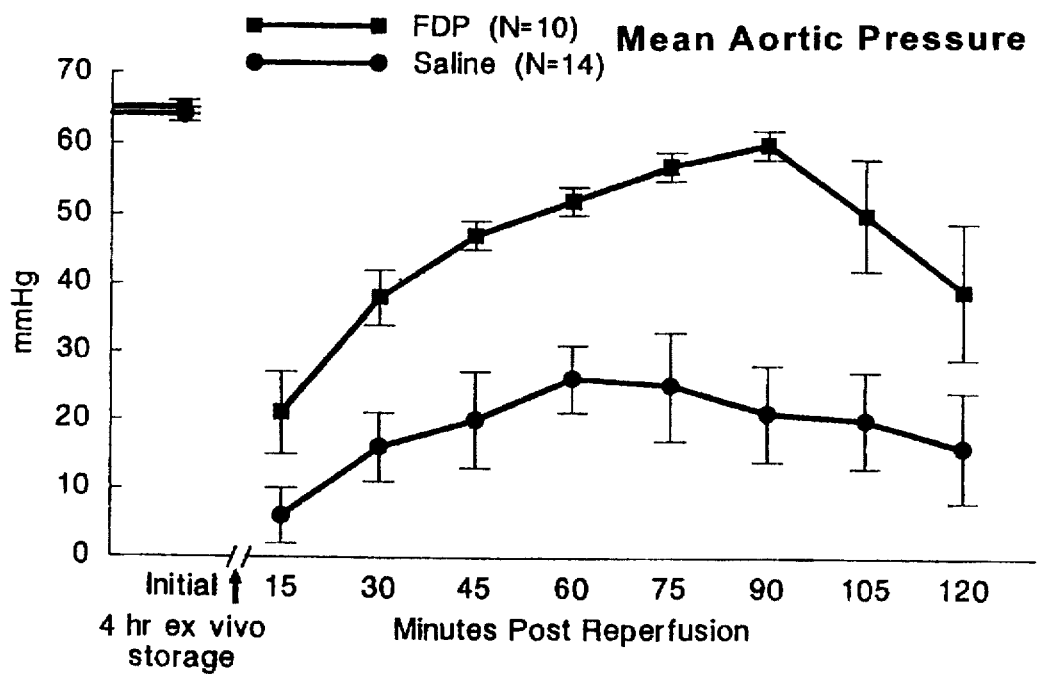
FIG. 3 is a graph depicting the improvement in mean aortic pressures provided by FDP treatment.
Figure 4:
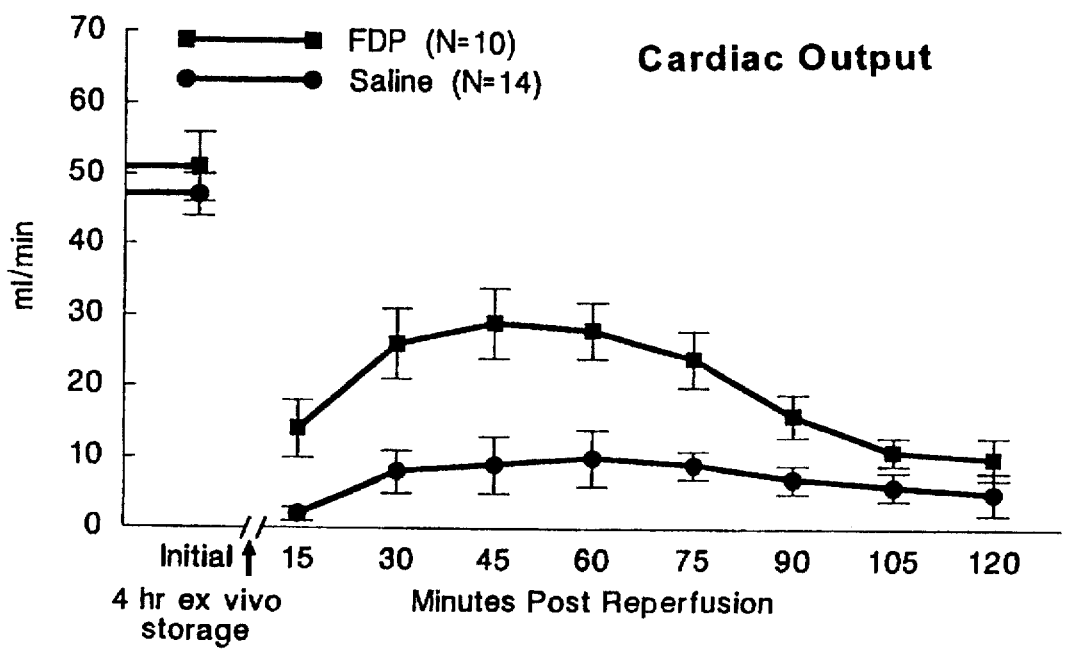
FIG. 4 is a graph depicting the improvement in cardiac output provided by FDP treatment.

This invention discloses a method of using fructose-1,6-diphosphate (FDP) to help suppress the rejection of internal organs such as kidneys, hearts, etc. At least three major advantages of FDP in conjunction with organ transplants have been identified: (1) FDP can help reduce the unwanted proliferation of certain types of stimulated lymphocytes which would otherwise pose a risk of attacking the non-self cells in the transplanted organ; (2) FDP can also potentiate the effectiveness of cyclosporine as a transplant-protecting immunosuppressant, thereby allowing a reduction in CSA dosages, which in turn can reduce the likelihood and the severity of toxic side effects and other dangers of CSA treatment; (3) FDP can also reduce the amount of damage inflicted on an organ during the removal and storage steps required in organ transplantation.

Each of these aspects of the invention will be discussed below under a separate heading.

In Vitro Tests on Stimulated T-lymphocytes

As mentioned in the Background section, activated T cells (also referred to as stimulated or sensitized T cells) play an important role in allograft rejection. If T cells are stimulated by non-self antigens on a transplanted organ, they can launch an attack which leads to rejection of the foreign organ.

It is known that within 30 seconds after addition of a mitogen to lymphocytes in culture, the transport of potassium ions ($K^+$) and sodium ions ($Na^+$) across the cell membrane is doubled, compared to unstimulated lymphocytes. This ion transport system, controlled by an enzyme known as sodium-potassium ATPase, is a vitally important cell function that maintains low sodium concentrations and high potassium concentrations inside cells (relative to extracellular fluid). In stimulated lymphocytes, the increased activity of ion pumps at the cell membrane consumes about 40% of the total energy being generated in the cell; this is an extraordinarily high fraction, and yet the significance of increased ionic transport in stimulated lymphocytes is not understood; it may represent a volume adjustment for the cells, which is characteristic of blast transformation, or it may be connected to changes in cyclic adenosine monophosphate (cAMP), since it is believed that activation of T lymphocytes requires an increase in cAMP concentration. Adenyl cyclase, the enzyme that converts ATP into cAMP, and $Na^+$-$K^+$-ATPase must compete against each other for energy-rich ATP supplies in stimulated T lymphocytes, and their stimulated activity levels contribute to a relatively rapid decrease in the ATP supplies in such cells.

FDP has been shown in many studies to help prevent $K^+$ loss and $Na^+$ influx into cells, in ischemic (anoxic or hypoxic) tissue; it has also been shown to help maintain adequate ATP concentrations for the $Na^+$ $K^+$-ATPase pump to function adequately under such conditions. Since roughly 40% of the total cell energy is used for ion transport in a healthy cell, and since a majority of that energy is produced in cytosol by glycolysis, the presence of FDP is likely to augment ATP production.

One who is aware of these facts might expect addition of FDP to increase the level of T lymphocyte stimulation, by providing the lymphocytes with an energy-rich substrate the cells can use to help them sustain or increase the level of stimulation. To investigate that question, and to study the effects of the entropic states of a cell on the stimulation process, the Applicant conducted experiments to determine whether addition of FDP would, in fact, increase the stimulation level of cells.

The results, however, indicated that the addition of FDP did not increase the stimulation level of the cells. Instead of providing an energy-rich substrate that the cells could use to help drive the stimulation activities, exogenous FDP actually decreased the level of lymphocyte stimulation.

The in vitro tests, and their results, are described in detail in Example 1. Briefly, T lymphocytes were obtained from rat spleens. The cells were then stimulated by Concanavalin A (ConA), a mitogen that specifically stimulates T lymphocyte replication, both in control samples and in samples that were also contacted with either FDP or cyclosporine at various concentrations. Cell replication was measured by assaying the uptake of thymidine which had been radiolabelled using tritium, a heavy isotope of hydrogen. Cell viability was measured using a dye, trypan blue; intact and viable cells can exclude trypan blue from their interiors, while damaged or dead cells cannot.

The results, in Tables 1 and 2, indicated that FDP is as efficacious as cyclosporine in suppressing the mitogen-stimulated replication of T lymphocytes in vitro. At the same time, as shown in Table 3, FDP has either insignificant (at low dosages) or very mild (at higher doses) adverse effects on cell viability; by contrast, cyclosporine has substantial toxic effects on T cell viability.

These unexpected results showed that FDP, despite the fact that it provides an extra energy source, actually decreases rather than increases T cell stimulation.

TABLE 1

Inhibiting effect of FDP on Thymidine incorporation by Concanavalin A-stimulated T-lymphocytes

| Control | FDP 1:10000 | FDP 1:1000 | FDP 1:500 | FDP 1:250 | FDP 1:100 | FDP 1:10 |
|---|---|---|---|---|---|---|
| 166098 ± 37.622 | 89032 ± 17.953 | 62518 ± 15.072 | 52481 ± 19.287 | 24818 ± 8889 | 1175 ± 720 | 136 ± 37 |
| Significance N.S. | | $p < 0.05$ | $p < 0.025$ | $p < 0.005$ | $p < 0.005$ | $p < 0.005$ |

TABLE 2

Inhibitory effect of Cyclosporine A (CSA) on Thymidine incorporation by Concanavalin-A stimulated T-lymphocytes

| Control | CSA 0.5 ng/ml | CSA 5 ng/ml | CSA 50 ng/ml | CSA 500 ng/ml |
|---|---|---|---|---|
| 166098 ± 37.622 | 54841 ± 9928 | 32027 ± 4574 | 12956 ± 6450 | 294 ± 165 |
| Significance | N.S. | $p < 0.05$ | $p < 0.025$ | $p < 0.02$ |

TABLE 3

Comparison of the viability of FDP and CSA-treated rat spleen T-lymphocytes at 48 hours after incubation

| | % Viability | Significance |
|---|---|---|
| Control | 83.6 ± 4.12 | |
| FDP - 1:10000 | 83.3 ± 4.28 | N.S. |
| FDP - 1:1000 | 81.6 ± 4.14 | N.S. |
| FDP - 1:500 | 78.7 ± 3.87 | N.S. |
| FDP - 1:250 | 75.7 ± 4.5 | N.S. |
| FDP - 1:100 | 76.1 ± 3.72 | N.S. |
| FDP - 1:10 | 65.3 ± 5.0 | $p < 0.02$ |
| CSA 0.5 ng/ml | 69.55 ± 1.69 | $p < 0.01$ |
| CSA 5 ng/ml | 62.11 ± 2.74 | $p < 0.001$ |
| CSA 50 ng/ml | 53.0 ± 4.1 | $p < 0.0005$ |
| CSA 500 ng/ml | 42.66 ± 6.11 | $p < 0.00001$ |

In Vivo Tests On Transplanted Hearts

Since unwanted T cell stimulation is known to be a primary factor in causing allograft rejection, the results of the in vitro studies discussed above, showing that FDP can suppress T cell stimulation, led to a series of in vivo tests using heart transplantations in rats. These tests are described in detail in Example 2. Briefly, laboratory rats from a strain known as Lewis rats were used as recipients, while rats from a different strain known as Wistar-Furth were used as heart donors.

In the recipient animals, the native heart was not cut out and replaced by a new heart. Instead, the heart from the donor animal was implanted in the abdomen of the recipient, in a manner that causes blood to be pumped through the heart but which does not impose a blood-pumping load upon the implanted heart. This model provides a good test to determine whether the body will reject the foreign tissue, yet it avoids the extraordinary difficulties that would arise if the animal's native heart were cut out.

In the first round of tests, four treatment groups and one control group were established. The control group received no FDP. The four treatment groups were injected intravenously with 350 mg/kg of FDP 15 minutes prior to surgery, at a dosage of 350 mg/kg (i.e., 350 mg of FDP per kilogram of body weight). The treatment animals also received a 90 minute infusion of FDP during the operation, at a rate of 10 mg/kg/min. In addition to these "perioperative FDP" injections, the four treatment groups also received:

Group 1: a two hour postoperative injection of saline.

Group 2: a two hour postoperative injection of FDP and a supplemental injection every 12 hours (350 mg/kg)

Group 3: a two hour postoperative injection, and a supplemental injection every 8 hours (350 mg/kg)

Group 4: a two hour postoperative injection, and a supplemental injection every 6 hours (350 mg/kg)

This initial round of tests was not intended or designed to evaluate long-term survival, and no antibiotics were given to any of these animals.

The animals were examined daily for viability. If the transplanted heart did not have a palpable heartbeat, an animal was anesthetized and assessed. When the transplanted heart reached a level of non-viability, a lethal dose of pentobarbital was given, and the heart was removed, examined microscopically, and graded for rejection using the Stanford grading scale.

If a transplanted heart stopped beating prior to three days postoperatively, that animal was dropped from the study. Rats that died within five days of the operation for unknown causes were also dropped from the study. These deaths were believed to be secondary to sepsis, rather than caused by tissue rejection. Also, one animal in Group 1 died from a suture fracture; this animal was also dropped from the study.

The results are shown in Tables 4 and 5. In the control group, which did not receive FDP, the "mean survival time" (MST) was 7.6 days. All of these rats lived until the transplanted heart had been rejected, and their rejection grades ranged from moderate to severe/advanced.

Group I, which received perioperative FDP but no supplemental injections, had an MST of 13.5 days. The remainder of this group lived until rejection and had rejection grades from mild to severe/advanced. One rat that died from obvious sepsis was not graded for rejection, due to inadvertent disposal of the rat's body prior to grading.

Group II had a MST of 8.9 days. One rat died on the ninth day of apparent sepsis. All other rats lived until their grafts rejected and had rejection grades of mild to severe/advanced; the one mild grade belonged to the animal that died of apparent sepsis.

Group III had a MST of 10 days. One rat died on the 12th day of sepsis, and one with severe sepsis was euthanized in the evening of the 11th day; it was counted as a 12th day rejection because its graft was strongly palpable the night it was euthanized. The remainder of this group lived until rejection and had grades from moderate to severe/advanced.

Group IV had a MST of 9.6 days. All rats in this group lived until their grafts had rejected. They all had rejection grades of severe/advanced.

TABLE 4

Graft Survivals

| Study Group | N | Duration | Mean Survival Time MST ± SE | Significance |
|---|---|---|---|---|
| Control | 7 | 8,7,7,8,7,8,8 | 7.6 ± 0.2020 | |
| 1 | 11 | 16,10,9,25,16,15,8,12, 13,13,11 | 13.5 ± 1.4101 | p < 0.005 |
| 2 | 8 | 7,8,10,7,9,11,9,10 | 8.9 ± 0.5154 | p < 0.05 |
| 3 | 8 | 9,12,11,12,9,10,9.8 | 10.0 ± 0.5345 | p < 0.005 |
| 4 | 8 | 10,9,14,11,8,8,8,7 | 9.4 ± 0.8004 | p = 0.06 |

1 = perioperative injection
2 = bid injection
3 = tid injection
4 = qid injection

TABLE 5

Rejection Grades

| | N | Mild | Moderate | Severe/Advanced |
|---|---|---|---|---|
| Control | 7 | | 2 | 5 |
| *1 | 11 | 1 | 1 | 8 |
| 2 | 8 | 1 | 1 | 6 |
| 3 | 8 | | 1 | 7 |
| 4 | 8 | | | 8 |

*1 heart not evaluated secondary to inadvertent disposal.

As noted above, no antibiotics were given to any of these animals, and sepsis was a difficult problem facing this experiment. A total of four experimental rats (9.5%) died or were euthanized secondary to sepsis. All rats underwent two separate operations—one to place an internal jugular line, and one for the transplantation. The rats were then faced with continuous central cannulation and repeated injections. Aseptic techniques were used, but the rats tended to chew on their catheters and roll in their own feces. Accordingly, it was difficult to assure asepsis with this experimental group. However, despite these problems, these first-round tests demonstrated that FDP can prolong cardiac transplant survival in rats.

In Vivo Tests, Second Series

In a second series of in vivo tests, FDP alone and in conjunction with cyclosporine was tested for its ability to suppress allograft rejection and prolong survival of the transplanted heart. Cyclosporine-A (CSA) has become the cornerstone of most combination immunosuppressive protocols, but it presents intrinsic toxicities at immunosuppressive doses. Therefore, these tests evaluated FDP in conjunction with sub-optimal doses of CSA.

In these tests, the same procedure as described above was used to transplant hearts into the abdomens of recipient animals. Unlike the earlier tests, the animals also received prophylactic antibiotic treatment following surgery, as well as daily application of Bacitracin ointment of the site of the venous catheter.

The animals were divided into the following 6 groups:
Group I (n=6) received no FDP or CSA.

Group II (n=5) received only FDP as a preoperative injection of 350 mg/kg IV, and a perioperative infusion of 10 mg/kg IV for 90 min.

Group III (n=6) received a suboptimal dose of CSA, 2.5 mg/kg/day intramuscular (IM)

Group IV (n=5) received higher but still suboptimal doses of CSA (5 mg/kg/day IM)

Group V (n=5) received FDP as a preoperative injection (350 mg/kg IV) and perioperative infusion of 10 mg/kg/min for 90 min and supplemental injections of both FDP (350 mg/kg IV every 12 hours) and a suboptimal dose of CSA (2.5 mg/kg/day IM)

Group VI (n=5) received the FDP treatment as Group 5, and the CSA dose was increased to 5 mg/kg/day IM.

Groups III through VI received CSA for 7 days following the operation.

The results, shown in Table 6, indicate that FDP, by itself, can significantly prolong allograft survival. In the control group, which received no FDP or CSA treatment, the mean survival time (MST) averaged 7 days, while in the group that received FDP only, MST increased to an average of 11.4 days (statistical probability p<0.0001), which was comparable to the MST of the two groups that received CSA at 2.5 mg/kg/day (MST 12.0 days) or 5 mg/kg/day (MST 12.4 days). Just as importantly, the data for Groups 5 and 6, which received a combination of FDP and CSA, indicated even greater increases in MST's, to 17.6 days (CSA at 2.5 mg/kg/day) and 28.2 days (CSA at 5 mg/kg/day). This indicates that a combination of FDP and CSA significantly increased allograft survival, compared to either CSA or FDP alone.

Accordingly, the data from the two series of in vivo heart transplantation tests show that (1) FDP, by itself, can suppress allograft rejection and increase allograft survival times, and (2) FDP can also potentiate the useful immunosuppressive effects of cyclosporine, thereby allowing lower doses of cyclosporine to be used in a manner which can avoid or minimize the toxic side effects of cyclosporine. Both of these properties are highly useful in the long-term treatment of transplant recipients.

TABLE 6

Comparison of rat cardiac allograft survival given FDP alone, varying doses of CSA, and FDP/CSA in combination

| Dose mg/kg/day | N | Survival Time (Days) | MST ± SEM | Significance |
|---|---|---|---|---|
| Control No treatment | 6 | 6,7,7,7,7,8 | 7 ± 0.25 | |
| FDP pre and perioperative only | 5 | 10,10,11,12,14 | 11.4 ± 0.74 | p < 0.0001 |
| CSA 2.5 mg/kg/day | 6 | 10,11,12,12,13,14 | 12 ± 0.58 | p < 0.0001 |
| CSA 5 mg/kg/day | 5 | 10,11,13,14,14 | 12.4 ± 0.81 | p < 0.0001 |
| CSA 2.5 mg/kg/day FDP 700 mg/kg/day | 5 | 17,17,17,18,19 | 17.6 ± 0.4 | p < 0.000001 |
| CSA 5 mg/kg/day FDP 700 mg/kg/day | 5 | 26,27,27,30,31 | 28.2 ± 0.96 | p < 0.0000001 |

Reduction of Tissue and Cell Damage During Organ Storage

In addition to reducing the problems of allograft rejection after an organ has been transplanted into the body of a recipient, this invention also discloses that FDP can be used to minimize damage to an organ during the so-called storage period, after it has been removed from the body of a donor and until transplantation into a recipient. During this storage period, internal organs are usually kept in a hypothermic state (i.e., at reduced temperatures). Any temperature below normal body temperature of 37° C. is classified as hypothermic; in practice, organs being readied for transplantation are often chilled to a point slightly above freezing, using ice and saline slush, to minimize cellular metabolic demands without creating ice crystals inside the cells or organs.

Distant procurement of organs for transplantation is limited by the lack of ideal methods and agents for preserving the organs during any period they remain outside the body. Since ideal conditions and storage media have not been discovered, most organ transplants must be performed within a few hours after removal, and many transplants require extraordinary measures (such as specially chartered jet transportation) to reduce the storage and transportation period as much as humanly possible. The paucity of immunologically suitable donors for organs often makes distant procurement and transportation necessary, and even in cases which do not require transportation, some amount of time often elapses before a recipient can be contacted and prepared for surgery. For these and other reasons, more progress needs to be made in developing agents and methods that can reduce the amount of ischemic and other damage suffered by harvested organs during storage, transportation, and transplantation.

The primary cause for ischemic damage to harvested organ tissues is the failure of the oxidative metabolism. Under such circumstances, aerobic glycolysis is quickly exhausted, and anaerobic glycolysis commences in an effort to compensate for the inadequate aerobic energy production. After an initial increase in the catabolic activities of anaerobic glycolysis, anaerobic carbohydrate utilization begins to decline relatively quickly, due to increasing lactic acid, which has a number of adverse effects, including inactivation of the phosphofructokinase (PFK) enzyme which is necessary to carry out anaerobic glycolysis.

The failure of the oxidative metabolism during ischemic organ storage manifests itself and triggers additional problems in a variety of ways. The consequences, both during ischemic storage of organs and after blood flow has been re-established after transplantation, can contribute to partial or total loss of desired transmembrane ionic balances, enzyme release from the cells, generation of highly reactive and damaging oxidative free radicals, mitochondrial injury, and other adverse effects. In addition, after hypothermic ischemic storage, the ability of an organ to properly utilize oxygen during post-storage reperfusion is significantly depressed, due to mitochondrial injury by $Ca^{++}$ and generation of oxidative radicals during storage and after reperfusion. Not all of the mechanisms responsible for these alteration have not been precisely elicited, but it should be noted that two different and distinct factors contribute to the damage: (1) the damage caused by ischemia per se during the storage period, and (2) the damage caused by certain processes that begin or are manifested after perfusion with oxygenated blood has been reestablished. During ischemic hypothermic storage, despite the profound decrease in metabolic rates, there is still some level of breakdown and loss of ATP, which impedes the ability of Na-K-ATPase enzymes to carry out their ion pumping functions. This loss of energy required for transmembrane ion pumping leads to intracellular loss of $K^+$ and infiltration of $Na^+$, which results in edema (fluid accumulation and swelling) in the cells and organ, and in enzyme release and other injury to the cells and organ. The breakdown of ATP during ex vivo organ storage also produces metabolites which, upon reestablishment of blood flow after transplantation, provide substrates for the xanthine oxidase pathway, which produces toxic oxygen free radicals that randomly attack and destroy biomolecules, thus causing further injury to the tissue of the transplanted organ. The extent of oxidative radical damage and other forms of injury upon ischemically stored organs appears to depend upon the nature and severity of the ischemic insult (i.e. how long the organ was stored) and the presence of phagocytic cellular elements in the blood with which the organ is reperfused. There are suggestive experimental and clinical evidences that cells called polymorphonuclear neutrophils (PMN's) produce additional tissue injury in post ischemic reperfusion of organs. Once activated, PMN's undergo a "respiratory burst" characterized by an increase of oxygen consumption via the pentose phosphate pathway; this pathway can generate cytotoxic oxygen species which cause additional injury to cells and organs.

As described in Examples 4 and 5, it has been shown by the Applicant that exogenous FDP can alleviate these problems. FDP provides at least two distinct beneficial effects: (1) it helps stimulate activity of the PFK enzyme, by reversing lactate inactivation of the enzyme, and (2) it can directly provide a high energy substrate which supplies the glycolytic pathway downstream of the PFK enzyme. Since both of these factors help prolong and increase the glycolytic supply of energy-rich ATP to cells in an organ being stored ischemically, such intervention can attenuate tissue damage during storage of an organ outside the body.

As shown in FIGS. 1–5 (Example 4), FDP treatment led to substantial increases in the mechanical functions (heartbeat rate, systolic aortic pressures, mean pressures, and output rates) and myocardial ATP content in perfused hearts that had been subjected to 4 hours of cold ischemic ex vivo storage.

In addition, as described in Example 5, FDP treatment of ischemically stored livers, kidneys, and hearts also protected the mitochondria from injury, as evidence by significantly higher post-storage oxygen utilization.

These results clearly demonstrate that treatment with FDP significantly improved both the mechanical and the intracellular chemical condition of ex vivo stored hearts that were subjected to the type of ex vivo ischemic storage that transplanted organs often undergo.

Dosages and Modes of Administration

To take advantage of its organ-protecting and rejection-suppressing activities, FDP can be administered in several ways, and since it is actively consumed in the glycolytic process, the preferred mode of administration involves sequential administrations to ensure that an adequate supply remains available over a sustained period of time.

In one mode of administration, FDP is administered intravenously (via either bolus injection or continuous infusion) to the donor, prior to removal of the organ from the body of the donor. The donor can be a completely alive and competent person (such as a kidney donor), a person who is mortally injured or terminally ill and who is unconscious or comatose, or a person who has recently died and whose heartbeat must be stimulated externally through CPR-type external pressure or electrostimulation. If substantial blood circulation is still present in the patient's body, intravenous injection or infusion can be used to introduce FDP into the organ that will be removed and transplanted.

If no heartbeat is present, the organ should be removed from the body as quickly as possible, and its main arteries should be coupled to a perfusion device that will pump a suitable FDP-containing fluid (such as a phosphate-buffered saline solution that also contains glucose) through the blood vessels of the organ. If desired, the organ can also be submersed in a fluid which contains FDP, to allow permeation of FDP from the fluid into the superficial layers of organ tissue.

After the organ has been removed, if it is being sustained on perfusion equipment which provides continuous pumping of fluid through the organ, the fluid should contain FDP at a concentration in the range of about 0.5 to about 50 mg/ml. Alternately, if fresh fluid is pumped through the organ intermittently (such as every ten minutes), then the organ should receive a supply of FDP which provides about 50 to 350 mg of FDP per kilogram of organ weight during each hour of storage at 4° C.

During surgery to implant the organ into the body of the recipient, the recipient should receive FDP via continuous intravenous infusion throughout the surgery, and for some period of time after surgery (such as 90 minutes or more, which is regarded as peri-operative infusion), at a dosage of about 50 to 350 mg of FDP per kg of body weight per hour in an initial bolus over about 10–15 minutes, and then a constant infusion of about 0.5 to about 10 mg/kg/min while the patient is under anesthesia.

After the peri-operative period is over, the transplant recipient should receive about 200 to 1500 mg FDP per kg body weight per day (preferably administered intermittently, such as every six hours) during an initial recovery period (such as about 7 to 10 days for most patients).

After the initial recovery period has passed, the patient can be placed on a lower long-term maintenance dosage of FDP, preferably in conjunction with another immunosuppressive agent such as a cyclosporine compound.

FDP can also be administered in response to episodes of acute rejection. Today, such episodes are usually treated by administering increased levels of CSA along with anti-inflammatory drugs such as certain steroids, until the episode has subsided. Such treatments can be supplemented, or in some cases possibly rendered unnecessary, by administration of FDP as part of the regimen used to treat episodic rejection crises.

EXAMPLES

Example 1

In Vitro Tests on Stimulated T Lymphocytes

Sprague-Dawley rats (150–200 gm body weight) were euthanized by overdose of ketamine (injected intramuscularly, IM). Their spleens were removed under sterile conditions and placed in a plastic petri dish with Buffered Hanks Solution (BHS). The splenic parenchyma was torn apart with sterile needles and forceps. The solution with the splenic fragments was homogenized with a Teflon pestle in a glass tube. This allowed the cells to be expressed into the solution which was then filtered and placed over Ficoll-Hypaque and centrifuged at 1500 RPM for 20 minutes in order to separate mononuclear cells. The middle layer of cells (containing lymphocytes) was removed and centrifuged at 1000 RPM for 10 min. After removing the supernates, the remaining red blood cells were lysed with 0.83% $NH_4Cl$ solution, and the cells were again centrifuged at 1000 RPM for 2–3 min. The supernate was poured off and the cells were washed twice with BHS and then resuspended in tissue culture media (RPMI-1640 with 10% fetal calf serum). The cells then were adjusted to final concentration of $5 \times 10^6$ cells/ml with RPMI-1640 and 10% fetal calf serum.

A tissue culture multi-well plate was used for incubation. All well filling was done under sterile conditions. Each well received 0.1 ml of cell suspension, 0.1 ml of either FDP or Cyclosporine A (CSA) for inhibition of cell proliferation, and 0.1 ml of either Concanavalin A (ConA) (10 µg/ml mixed in RPMI-1640 cell culture media), or RPMI-1640 only (as a control). The well volume capacity was 0.35 ml. ConA is a known mitogen that stimulates proliferation of T cells; these tests were designed to evaluate the effects of either FDP or CSA on mitogen-induced T cell stimulation.

Six different dilutions (freshly prepared in sterile water solution from 10% FDP stock solutions) were used—1:10, 1:100, 1:250, 1:500, 1:1000 and 1:10000. The four concentrations of CSA (50 mg/ml stock) used were 0.5, 5, 50, and 500 ng/ml. CSA, FDP, and ConA were diluted with RPMI-1640. A few wells were used to measure the stimulation index, and received ConA or RPMI without FDP or Cyclosporine. All combinations were run in triplicate. The wells were labeled and incubated with $CO_2$ at 35° C. for 48 hours.

Each well then received 0.05 ml of tritiated ($^3H$) thymidine (1 µCi/0.05 ml). Radiolabelled thymidine is taken up by proliferating lymphocytes, allowing them to be counted using a liquid scintillation counter. After 16 to 20 hours of incubation the samples were harvested onto glass filter paper strips using a multiple automated sample harvester. The paper was allowed to dry 4–5 hours. Paper from each well was placed in scintillation counting vials with 5 ml fluorane (scintillene). Each sample was counted for 2 minutes, and results were reported in counts per 2 minute period, plus or minus a standard error measured over 13 experiments (for FDP) or 9 experiments (for CSA), each experiment involving triplicate samples. Significance was assessed by unpaired t-test.

Cell viability in each combination was checked after 48 hours of incubation, using a trypan blue dye exclusion test. The results of the cell viability tests are in Table 3, which indicates percentages of cells that were viable.

As shown in Tables 1 and 2, the results indicate that the proliferation of rat spleen T-lymphocytes was inhibited by both FDP and Cyclosporine-A in a dose-dependent manner when these cells were stimulated with concanavalin A. As shown in Table 3, the viability of the lymphocytes exposed to FDP was higher than for cells incubated with CSA. FDP, although it significantly suppressed T-lymphocyte transformation, did not significantly damage the viability of the cells except at very high concentrations. By contrast, CSA reduced lymphocyte viability at all concentrations tested.

In summary, the data indicate that FDP is as efficacious as CSA in suppressing transformation of stimulated T lymphocytes in vitro, while causing little or no damage to cell viability.

Example 2

In Vivo Tests Using Transplanted Hearts (Series 1)

Male Wistar-Furth rats (WF;RT-1$^u$) and male Lewis rats (Lew;RT-1$^1$) were obtained from Harlan Sprague-Dawley Animal Laboratories. Lewis rats weighing (200–224 gm) were used as recipients. WF rats weighing (200–224 gm) were used as donors.

The Lewis rats were anesthetized with a mixture of ketamine (100 mg/kg) and xylocaine (5 mg/kg) by intraperitoneal injection (IP) 1 to 2 days prior to transplantation. At this time, PE-90 tubing was placed in the internal jugular vein and brought out through the posterior aspect of the neck. The rats were placed in individual cages to prevent dislodging of the catheter. No limits were placed on water or rat chow.

The transplantation procedure was a modified version of Ono and Lindsey's microvascular technique for intra-abdominal transplantation. WF rats were anesthetized with pentobarbital (50 mg/kg). The chest and abdomen were shaved and prepped with betadine and then placed on a thermostatically controlled operating platform. A mid-line abdominal incision was made and 300 units of heparin was injected into the inferior vena cava (IVC). After three minutes, the sternum and anterior chest were separated from the diaphragm and lateral ribs with heavy scissors. The chest cavity was opened and the IVC was ligated using a 5-0 silk ligature. The aorta was then dissected out and cross clamped at the level of the innominate artery. Three cc of cold cardioplegia solution (4° C.) was injected into the aortic root with a 25 gauge needle. The aorta was divided below the clamp. The pulmonary artery was dissected free and divided at its bifurcation. A 2-0 silk ligature was placed around the heart and the superior vena cava and pulmonary veins were ligated en mass. The heart was then removed and placed in iced saline with heparin (2 units/ml).

Lewis rats were then anesthetized in a similar fashion. After shaving and prepping the abdomen, a mid-line incision was made. The IVC and the infrarenal aorta were mobilized together. A curved bulldog was then used to cross clamp the vessels. The anastomosis was sewn between the pulmonary aorta and IVC using a 9-0 Ethicon microsurgical suture. The aorta-aorta anastomosis was then performed in a similar end-side fashion. The suture line was then surrounded by Avitine and the clamp was removed slowly. The hearts became pink and started actively contracting in 20–30 seconds. The abdominal contents were then replaced and the abdomen was closed with 2-0 silk suture.

Four treatment groups and one control group were then established. The experimental groups were injected with 350 mg/kg of FDP IV 15 minutes prior to surgery. They then received a 90 minute infusion of FDP during the operation at a rate of 10 mg/kg/min. No antibiotics were given to any of the animals in this study.

The experimental groups received either:
1) Perioperative FDP followed by a two hour postoperative injection of saline.
2) Perioperative FDP followed by a two hour postoperative injection and then every 12 hour injection (350 mg/kg)
3) Perioperative FDP followed by a two hour postoperative injection and then every eight hour injection (350 mg/kg)
4) Perioperative FDP followed by a two hour postoperative injection and then every six hour injection (350 mg/kg)
The control group received no injection.

The animals were examined daily for viability. When the heart beat was no longer palpated, they were anesthetized with ketamine/xylocaine and assessed under anesthesia. If the transplanted heart was non-viable, a lethal dose of pentobarbital was given. The hearts were harvested and placed in 10% formaldehyde. They were then examined microscopically and graded for rejection using the Stanford grading scale.

Any heart that stopped prior to three days postoperatively were considered technical problems and dropped from the study. Rats that died within five days of the operation for unknown cases were also dropped from the study. These deaths were felt to be secondary to sepsis. There was also one rat that died at eight days from a suture fracture. This rat was also dropped from the study.

The Mean Survival Time (MST) of the control group was 7.6 days (Table I). All of these rats lived until the transplanted heart had rejected. Their rejection grades ranged from moderate to severe/advanced (Table II).

Group I had a MST of 13.5 days (Table I). One rat died at eight days from a fractured suture and was dropped from the study. A second rat died on the ninth day of sepsis. The remainder of this group lived until rejection and had rejection grades from mild to severe/advanced (Table II). the rat that died of sepsis was not graded secondary to inadvertent disposal of the rat.

Group II had a MST of 8.9 days (Table I) One rat died on the ninth day of sepsis. All other rats lived until their grafts rejected and had rejection grades of mild to severe/advanced (Table II). The one mild grade belonged to the transplant that died of sepsis.

Group III had a MST of 10 days (Table IV). One rat died on the 12th day of sepsis and one was put down in the evening of the 11th day with sepsis. The second rat was counted as a 12th day rejection because its graft was strongly palpable the night it was put down. The remainder of this group lived until rejection and had grades from moderate to severe/advanced (Table V).

Group IV had a MST of 9.6 days (Table IV). All rats in this group lived until their grafts had rejected. They all had rejection grades of severe/advanced (Table V).

Sepsis was a difficult problem facing this experiment. A total of four experimental rats (9.5%) died or were put down secondary to sepsis. All rats underwent two separate operations—one to place the internal jugular line and one for the transplantation. The rats were then faced with continuous central cannulation and repeated injections. Aseptic techniques were used but the rats chewed on their catheters and rolled in their own feces. It was difficult to assure asepsis with this experimental group.

Despite the above problems, the study demonstrates that FDP will prolongs cardiac transplant survival in rats.

Example 3

In Vivo Tests Using Transplanted Hearts (Series 2); Increasing Allograft Survival with FDP Alone and in Combination with Cyclosporine The surgical technique used in these tests was exactly the same as described in Example 2, except the animals in this series of tests received prophylactic antibiotic treatment following surgery, and daily application of Bacitracin ointment of the site of the venous catheter.

The animals were divided into the following 6 groups:

Group I (n=6), the controls, received no FDP or CSA.

Group II (n=5) received only FDP as a preoperative injection of 350 mg/kg IV, and a perioperative infusion of 10 mg/kg IV for 90 min.

Group III (n=6) received suboptimal dose of CSA (2.5 mg/kg/day IM).

Group IV (n=5) received higher suboptimal doses of CSA (5 mg/kg/day IM).

Group V (n=5) received FDP as a preoperative injection (350 mg/kg IV), perioperative infusion of FDP at 10 mg/kg/min for 90 min, and maintenance injections of FDP (350 mg/kg IV every 12 hours). This group also received CSA, at 2.5 mg/kg/day IM.

Group VI (n=5) received the same FDP treatment as Group 5, and the CSA dose was increased to 5 mg/kg/day IM.

Groups III through VI received CSA for 7 days following the operation.

Individually, both FDP and CSA significantly prolonged allograft survival, as shown in Table 6. In Group 1 (controls), which received no FDP or CSA treatment, MST was 7.0±0.25 days. In Group 1, which received FDP only, MST was 11.4±0.74 days (statistical probability p<0.0001). In Group 2, which received CSA at 2.5 mg/kg/day, MST was 12.0±0.57 days (p<0.0001). In Group 3, with CSA administered at 5 mg/kg/day, MST was 12.4±0.81 days (p<0.0001). There was no significant difference in allografts survival between the groups treated with FDP alone and those rats receiving CSA at either the 2.5 mg/kg/day or 5 mg/kg/day doses.

The data for Groups 1–4 indicate that FDP, by itself, has a substantial effect in reducing allograft rejection.

The data for Groups 5 and 6 showed a substantial increase in MST's, to 17.6 days and 28.2 days, respectively. This indicated that the combination of FDP and CSA significantly increased allograft survival compared to either CSA or FDP alone.

The accumulated data show that (1) FDP, by itself, can decrease the problem of allograft rejection and increase allograft survival times, and (2) FDP can also potentiate the useful immunosuppressive effects of cyclosporine, thereby allowing lower doses of cyclosporine to be used in a manner which can avoid or minimize the toxic side effects of cyclosporine. Both of these properties are highly useful in the maintenance and treatment of transplant recipients.

In summary, it has been shown in both in vivo and in vitro tests that FDP possesses significant activity in reducing T cell proliferation and in prolonging the survival of allograft tissue. In addition, this novel immunosuppressant apparently avoids the toxicity problems that are inherent in all other agents that are presently being used to treat allograft rejection. If used in combination therapy, FDP can allow lower doses of other, more dangerous immunosuppressive agents (such as cyclosporine) to be used.

Example 4

Use of FDP to Reduce Damage During Organ Storage

Hearts were harvested from ketamine-anesthetized Sprague Dawley rats (350–450 gm body weight). Prior to harvesting the hearts, 17 randomly chosen rats received an intravenous bolus injection of FDP 450 mg/kg (10%). The hearts were removed, the left atria and aorta were attached to a modified Langendorf apparatus within 3 min, and the hearts were perfused ex vivo for 15 min at 37° C. with Krebs-Henseleit solution to which 0.07 mg/ml of FDP had been added. Rats in the control group (n=21) received an equivalent volume saline injection prior to surgery, and the hearts were perfused for 15 min with Krebs-Henseleit solution containing no FDP. Heart rates, systolic and diastolic pressures, cardiac outputs, and coronary blood flow during this period were measured and recorded.

After the 15 minute perfusion period, the control hearts (n=21) were flushed with cardioplegic solution (Isolyte, $K^+$ 20 mEq/L). The FDP=treated hearts (n=17) were flushed with the same solution containing 1 mg/cc of FDP. The hearts were respectively placed in cold (4° C.) saline solution, with 0.9% NaCl or 0.9% NaCl containing 1 mg/ml FDP, and stored at 4° C. for 4 hours. After the 4 hour storage period was completed, the hearts were reperfused and warmed to 37° C. again. Seven hearts from each group were taken out of the Langendorf apparatus after 15 minutes and analyzed for myocardial ATP content. The remaining hearts (10 in the treatment group, and 14 in the control group) were measured in various ways (heartbeat rates, mean aortic and systolic pressures, and cardiac output) for 2 hours following the commencement of reperfusion.

Prior to cold ex vivo storage, the heart rates, mean aortic and systolic pressures, and cardiac output were not significantly different between the control and treatment groups.

Figure 5:
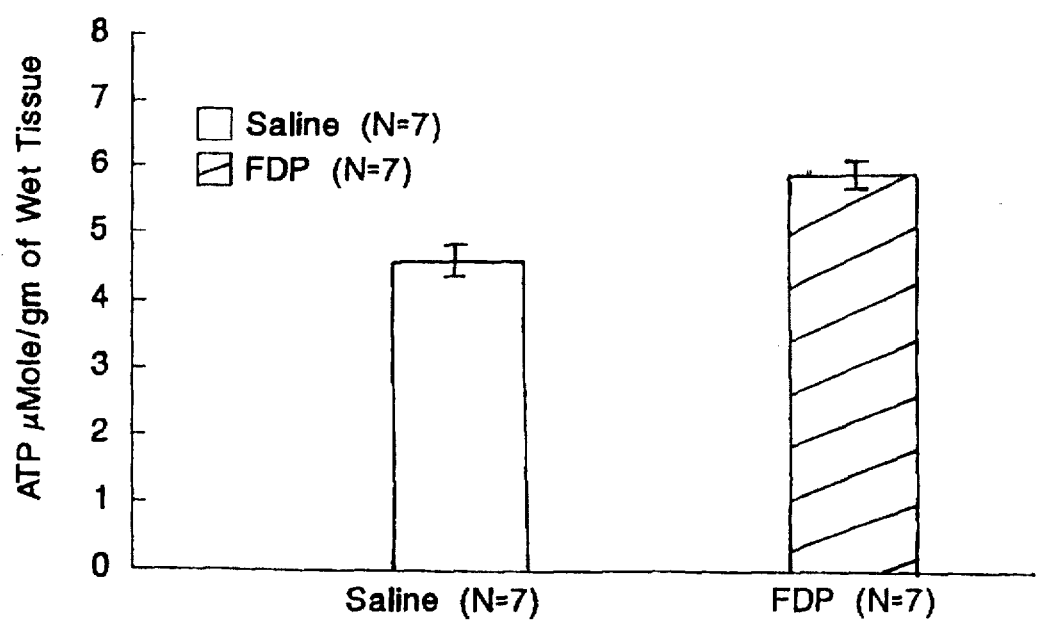
FIG. 5 is a graph depicting the increase in myocardial ATP levels provided by FDP treatment.

After 1 hour and 30 min of reperfusion, all FDP-treated hearts (n=10) still showed a heartbeat, while only 5 of the 14 control hearts (p<0.005) showed a heartbeat. The post-storage heartbeat rate (FIG. 1), peak systolic aortic pressures (FIG. 2), mean pressures (FIG. 3), and cardiac output rates (FIG. 4) were all significantly higher for the FDP-treated hearts than for the control group. The myocardial ATP content after 15 min of reperfusion was also higher in FDP-treated hearts than in the control group (FIG. 5; p<0.01).

These results clearly demonstrate that treatment with FDP significantly improved the mechanical function of ex vivo stored hearts and increased the myocardial ATP levels after 4 hours of ex vivo hypothermic ischemic storage.

Example 5

Protection Against Mitochondrial Injury Using FDP in Ex-vivo Stored Organs

As previously indicated, after a period of hypothermic ischemic storage, the ability of an organ to utilize oxygen following post-ischemic reperfusion is impaired. This is due to mitochondrial damage by $Ca^{++}$ and to the creation of damaging oxidative radicals during storage and following reperfusion.

Since the mechanical function and myocardial ATP content was significantly improved in the hearts treated with FDP before and during ischemic storage, an additional set of experiments were conducted in which the oxygen consumption in organs after 16 to 20 hours of hypothermic ischemic storage was assessed.

Sprague Dawley rats (150–180 gm/body weight) were anesthetized with Ketamine 35 mg/kg. The liver, kidney and heart were excised and placed in 50 ml of a standard cardioplegia solution sold under the trademark ISOLYTE (which contained $Na^+$-41 mEq/L, $K^+$-16 mEq/L, $Ca^{++}$-5 mEq/L, $Mg^{++}$ 3 mEq/L, $Cl^-$-40 mEq/L, acetate 24 mEq/L with 5% Dextrose), precooled to 4° C. To half of the storage containers, 1 mg/ml of 10% FDP was added; to the rest of the containers, a similar amount of glucose was added. The containers were placed on ice in a refrigerator. After storage for 16 to 20 hours, the organs were weighed and placed in a metabolic chamber for determination of oxygen consumption, using a Clark polarographic electrode. The total volume of the chamber was 10 ml and the composition of the medium was 8 ml phosphate buffered saline (PBS Dulbecco, $Mg^{++}$ and $Ca^{++}$ free) and 2 cc of Dextrose at a temperature of 36°±0.2° C. The organ was placed in the chamber and 100% oxygen was bubbled for 45 sec. The partial pressure of the dissolved oxygen was usually 480–560 mm Hg. Then the chamber was sealed hermetically, and $O_2$ consumption by the organ was recorded on a strip chart recorder at a speed of 1 cm/min. Initial and final $PO_2$ levels of medium in the chamber were measured on a Radiometer Blood Gas Analyzer Model ABL-4.

The oxygen consumption levels after ischemic storage (17.62±0.22 hours) for the FDP-treated livers (n=12) was 76.7±4.4 $O_2$ mmHg/min/gm at 36.4° C., compared to levels of 55.5±4.8 in control livers (n=12) (p<0.005). Similarly, FDP-treated kidneys (n-11) had significantly better post-storage $O_2$ consumption (74.15±4.8 mmHg $O_2$/min/gm) than control kidneys (n=11; 57.4±4.6 mmHg $O_2$/min/gm, p<0.025). FDP-treated hearts (n=4) also had better post-storage $O_2$ consumption, 68.4±3.14 mmHg $O_2$/min/gm, compared to 46.2±6.5 for controls hearts (n=4; p<0.025).

These data clearly show that treatment of ischemically stored organs using FDP not only preserves to a significant degree the mechanical function of hearts following hypothermic ischemic storage, but also protects the mitochondria from injury, as evidence by significantly higher post-storage oxygen utilization.

Thus, there has been shown and described a new and useful method for using FDP to reduce the problem of allograft tissue rejection. Although this invention has been exemplified for purposes of illustration and description by reference to certain specific embodiments, it will be apparent to those skilled in the art that various modifications and alterations of the illustrated examples are possible. Any such changes which derive directly from the teachings herein, and which do not depart from the spirit and scope of the invention, are deemed to be covered by this invention.

I claim:

1. A method of suppressing an allograft rejection response in a recipient of transplanted tissue, comprising the administration of:

(a) a cyclosporine compound, at a pharmacologically acceptable dosage which is effective in suppressing a T-type lymphocyte cell activation response after an organ transplant operation; and, (b) fructose-1,6-diphosphate, at a pharmacologically acceptable dosage which acts in a synergistic manner with the cyclosporine compound, thereby reducing the dosage of the cyclosporine compound which is required to effectively suppress a T-type lymphocyte cell activation response after an organ transplant operation.

2. The method of claim 1 wherein the fructose-1,6-diphosphate is administered to the patient via intravenous infusion after an organ transplant operation.

3. A method of suppressing an allograft rejection response in a recipient of transplanted tissue, comprising administering, to a mammalian recipient of transplanted tissue, a combination of (a) fructose-1,6-diphosphate, and (b) a cyclosporine compound which is a known immunosuppressive agent that suppresses proliferation of activated T cells, wherein the fructose-1,6-diphosphate is administered in a pharmacologically acceptable dosage which synergistically increases the immunosuppressive activity of the cyclosporine compound, thereby allowing a lower dosage of the cyclosporine compound to be used, to provide effective immunosuppressive results while reducing any toxic side effects of the cyclosporine compound.

* * * * *